(12) United States Patent
Chou et al.

(10) Patent No.: US 11,951,259 B2
(45) Date of Patent: Apr. 9, 2024

(54) MEDICAL TUBE FOR USE WITH USER INTERFACE IN RESPIRATORY THERAPY

(71) Applicant: FOXXMED LTD., Yilan County (TW)

(72) Inventors: Jeng-Yu Chou, Yilan County (TW); Yung-Yang Shih, Yilan County (TW); Wen-Hsien Liu, Yilan County (TW)

(73) Assignee: FOXXMED LTD., Yilan County (TW)

( * ) Notice: Subject to any disclaimer, the term of this patent is extended or adjusted under 35 U.S.C. 154(b) by 409 days.

(21) Appl. No.: 17/218,163

(22) Filed: Mar. 31, 2021

(65) Prior Publication Data
US 2022/0313937 A1  Oct. 6, 2022

(51) Int. Cl.
| | |
|---|---|
| A61M 16/06 | (2006.01) |
| A61M 16/00 | (2006.01) |
| A61M 16/08 | (2006.01) |
| A61M 16/10 | (2006.01) |
| A61M 16/16 | (2006.01) |

(52) U.S. Cl.
CPC .... *A61M 16/0672* (2014.02); *A61M 16/0003* (2014.02); *A61M 16/0875* (2013.01); *A61M 16/1095* (2014.02); *A61M 2016/0027* (2013.01); *A61M 16/161* (2014.02); *A61M 2205/3334* (2013.01); *A61M 2205/3368* (2013.01)

(58) Field of Classification Search
CPC .......... A61M 16/0875; A61M 16/1095; A61M 39/08; A61M 2039/082; A61M 2039/0672; F16L 11/112
See application file for complete search history.

(56) References Cited

U.S. PATENT DOCUMENTS

| | | | |
|---|---|---|---|
| 6,367,510 B1 * | 4/2002 | Carlson | A61M 16/08 138/121 |
| 2003/0183294 A1 * | 10/2003 | Carlson | A61M 16/08 138/133 |
| 2018/0296787 A1 * | 10/2018 | Maurer | A61M 16/0611 |
| 2020/0289780 A1 * | 9/2020 | Kemps | A61M 16/109 |
| 2021/0077765 A1 * | 3/2021 | Peiris | A61M 16/1095 |
| 2022/0072260 A1 * | 3/2022 | Virr | A61M 16/0003 |
| 2022/0273902 A1 * | 9/2022 | Petrochenko | A61M 16/1095 |

FOREIGN PATENT DOCUMENTS

WO    WO-2022060231 A1 *   3/2022

* cited by examiner

*Primary Examiner* — Kendra D Carter
*Assistant Examiner* — Mautin I Ashimiu
(74) *Attorney, Agent, or Firm* — NZ CARR LAW OFFICE

(57) ABSTRACT

Disclosed herein are novel designs of a medical tube for delivering a respiratory gas to a subject in respiratory therapy, wherein the medical tube is in fluid connection with a user interface and a respiratory device. The medical tube has a tubular body, a first rib helically extending along the outer surface of the tubular body, and optionally, a second rib disposed next to the first rib, and optionally, a membrane encapsulating the first and/or second ribs thereby creating a helical space along the outer surface of the tubular body. In some embodiments, the first rib has a lumen and at least one wire disposed outside the lumen. In other embodiments, the first rib is free of any lumen and includes one or more wires extended therethrough. The lumen of the first rib or the helical space created by membrane encapsulation is configured to monitor the temperature, humidity, flow rate or pressure of the respiratory gas or an exhaled/inhaled gas of a subject.

8 Claims, 9 Drawing Sheets

MEDICAL TUBE FOR USE WITH USER INTERFACE IN RESPIRATORY THERAPY

BACKGROUND OF THE INVENTION

1. Field of the Invention

The present invention relates to novel designs of a medical tube, which is suitable for use in respiratory therapy for the delivery of a stream of gas during respiratory therapy.

2. Description of Related Art

A medical tube is commonly used with the respiratory device and user interface in respiratory therapy for delivering a respiratory gas to patients in need of assisted respiration. During operation, the respiratory device provides a stream of the respiratory gas at a pressure typically greater than the atmospheric pressure to the subject. To ensure the flow of the respiratory gas is delivered within certain desired parameters, various sensors may be disposed along the passages of the respiratory gas and/or exhale gas of a subject, so as to timely adjust the amount of the respiratory gas intended to be delivered.

The present invention are improved designs of a conventional medical tube, in which the, flow rate, pressure, and/or humidity of the respiratory gas, and/or exhaled gas and/or inhaled gas of a subject are monitored from places (e.g., the lumen of a rib, or a helical space along the outer surface of the medical tube) other than those commonly known in the existing art (e.g., in the medical tube or the respiratory device).

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a medical tube for delivering a respiratory gas to a subject in respiratory therapy, in which the medical tube is in fluid connection with a user interface and a respiratory device. The medical tube comprises in its structure, a tubular body and a first rib helically extending along the outer surface of the tubular body. The tubular body is configured to deliver the respiratory gas from the respiratory device to the user interface. The first rib has in its structure, a lumen and at least one wire, in which the lumen is in fluid connection with the user interface and the respiratory device, and the wire is disposed outside the lumen and is configured to heat the respiratory gas within the tubular body, and/or to detect the temperature, humidity, flow rate or pressure of the respiratory gas within the tubular body.

According to optional embodiments of the present disclosure, the first rib may further comprise one or more ridges independently extending out from the first rib. In certain embodiments, the second rib is disposed next to the first rib, and is solid inside. According to another embodiment, the second rib comprises at least one wire configured to heat the respiratory gas within the tubular body, and/or to detect the temperature, humidity, flow rate or pressure of the respiratory gas within the tubular body.

According to optional embodiments, the medical tube may further comprise a joint tube disposed at the free ends or the outer surface of the tubular body thereby allowing the joint tube to be in fluid connection with the lumen of the first rib.

According to optional embodiments, the medical tube may further comprise a membrane encapsulating the first rib, thereby generating a helical space along the outer surface of the tubular body. In non-limiting embodiments, the first rib may or may not have the lumen.

In another aspect, the present disclosure is directed to a respiratory system for use in a respiratory therapy of a subject. The respiratory system has the medical tube in any of the embodiments described above, a user interface, and a respiratory device. The user interface is in fluid connection with the medical tube. The respiratory device fluidly and electrically connects with the medical tube, wherein the respiratory device is configured to provide the respiratory gas and detect the flow rate or pressure of an exhaled gas and/or inhaled gas of the subject within the lumen or the helical space.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

Figure 1:
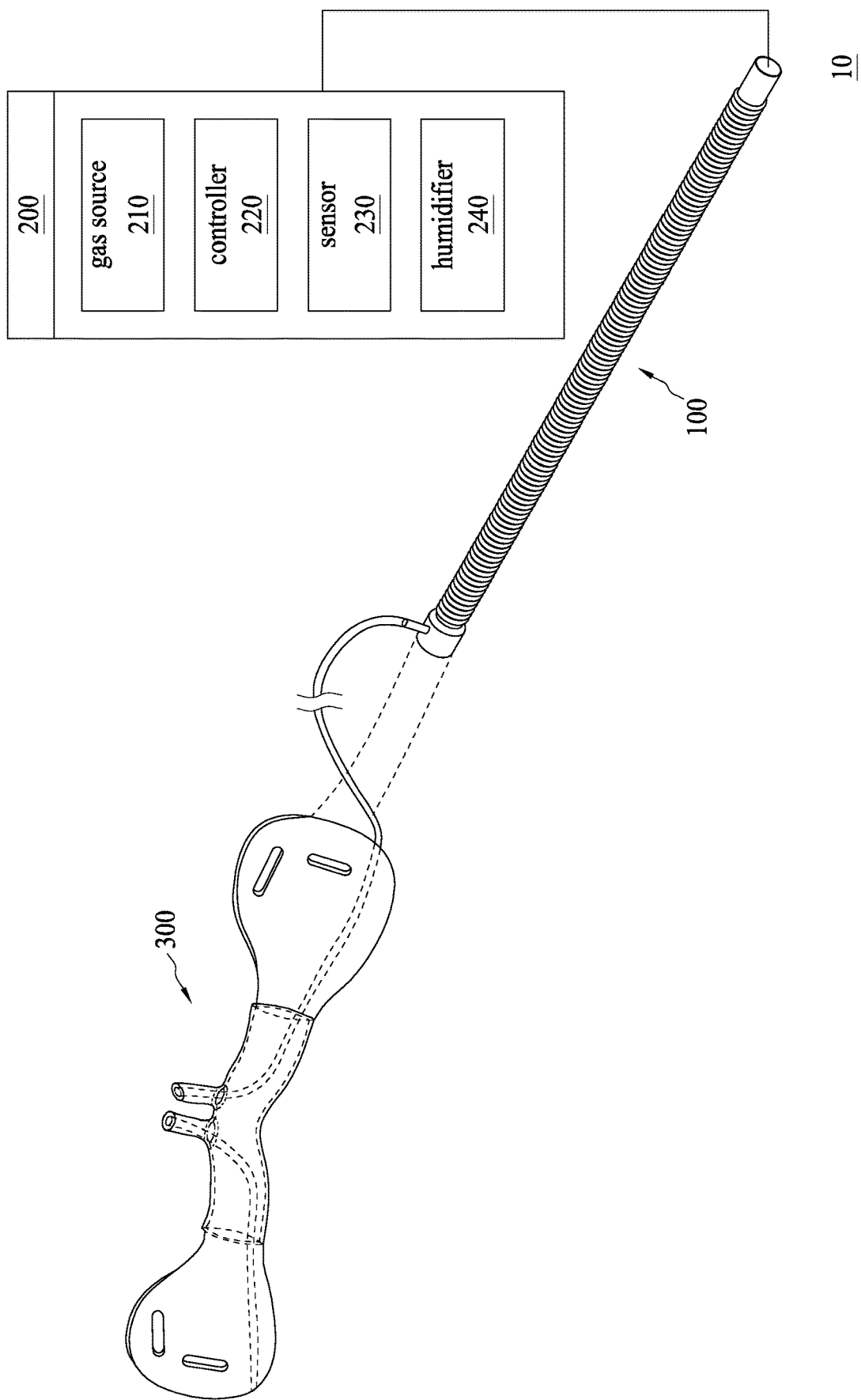
FIG. 1 is a schematic diagram of a respiratory system 10 for providing a respiratory gas to a user during respiratory therapy in accordance with one embodiment of the present disclosure.

FIG. 1 is a schematic diagram illustrating the respiratory system 10 for providing a stream of respiratory gas to a subject during respiratory therapy. The respiratory system 10 typically includes at least, a respiratory device 200 and a user interface 300 respectively coupled by a medical tube 100. Preferably, the respiratory device 200, the user interface 300 and the medical tube 100 are electrically and fluidly connected to each other. The user interface 300 may be any one of the user interface known to a skilled artisan, includes, but not limited to mask, cannula, and nasal pillow. For example, the mask may be a tracheal mask, face masks or nasal masks. In one embodiment, the user interface 300 may be any one of the nasal cannula known to a skill artisan, such as the one described in Taiwan Utility model NO. M576054U, which is incorporated herein by reference in its entity. As to the respiratory device 200, it may be any respiratory device known and used by skilled artisans in this field. The respiratory device 200 in general may include components and circuits for modulating the stream of respiratory gas to be delivered to its intended subject. Typically, the respiratory device 200 may comprise a respiratory gas source 210, a controller 220, a plurality of sensors 230, and a humidifier 240 electrically connected to each other, so as to provide a stream of respiratory gas (e.g., oxygen or air) at a pre-determined pressure, flow rate, temperature and/or humidity to the subject via the medical tube 100 and the user interface 300.

1. The Present Medical Tube

Figure 2A:
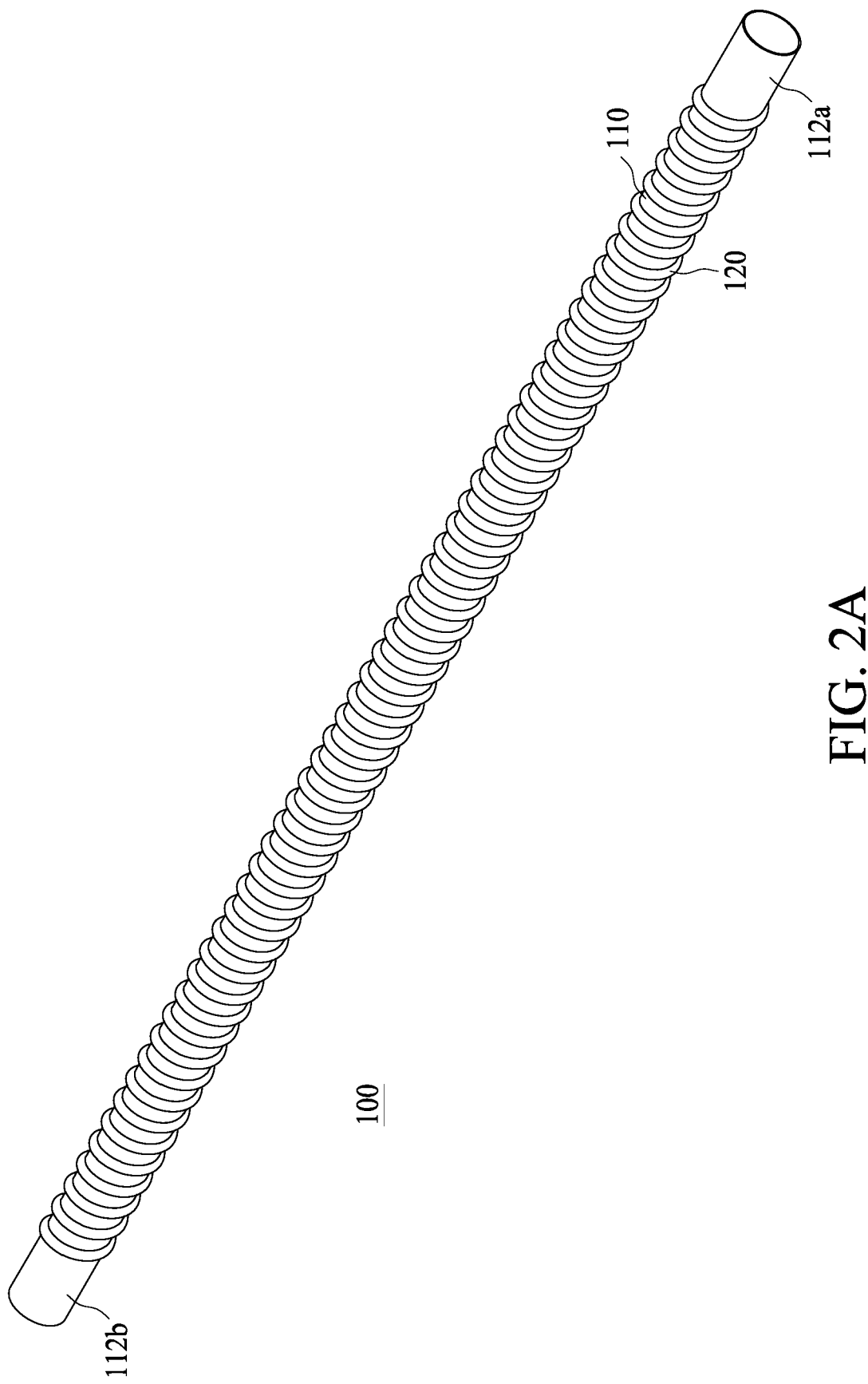
FIG. 2A is a schematic diagram of the medical tube 100 of FIG. 1
Figure 2B:
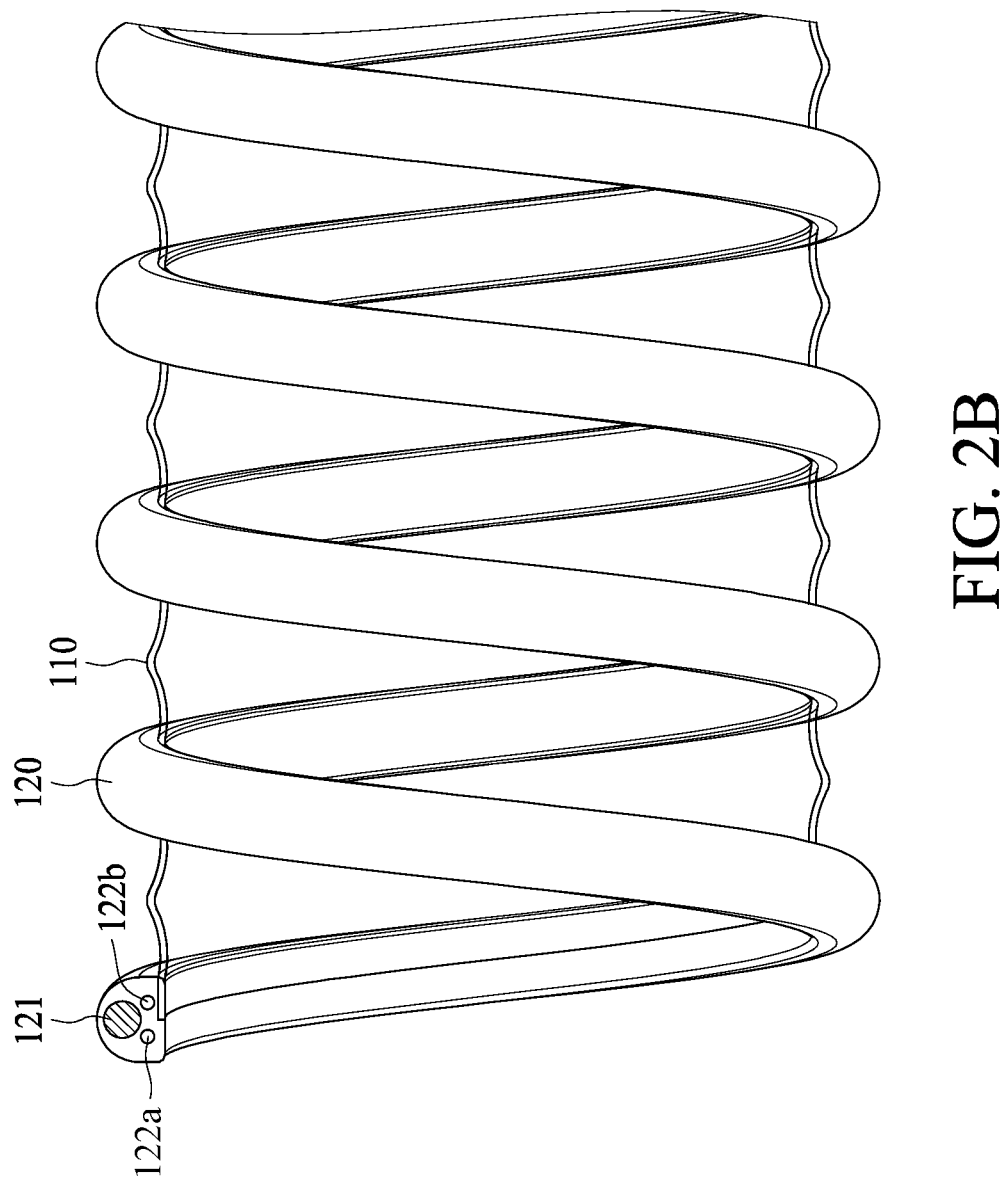
FIG. 2B is a schematic diagram of a portion of the medical tube 100 of FIG. 2A revealing the first rib 120 in cross section.

Reference is first made to FIG. 2A, which is a schematic diagram illustrating the present medical tube 100. The medical tube 100 includes in its structure, a tubular body 110 and a first rib 120 helically wrapped around the outer surface of the tubular body 110. Preferably, the tubular body 110 is hollow inside and has two ends 112a, 112b, preferably smoothbore ends, for easy connection with another component (e.g., an adaptor, a joint tube, and etc.) and/or device (e.g., the user interface 300, the respiratory device 200 and etc.). The first rib 120 has a lumen 121 and one or more wires 122 (e.g., 1, 2, 3, 4, 5, 6, 7, 8, 9 or 10 wires) independently extending the entire length of the first rib 120 (FIG. 2B). Preferably, the lumen 121 is in fluid connection with the respiratory device 200 and the user interface 300 and of FIG. 1, thus may serve as a channel for monitoring the pressure or flow rate of the exhaled gas and/or inhaled gas from the subject; while the one or more wires 122 are independently configured to heat the respiratory gas within the tubular body 110, and/or to detect the temperature, humidity, flow rate or pressure of the respiratory gas within the tubular body 110. According to non-limiting embodiment, the wires 122 are also configured to detect the temperature, humidity, flow rate or pressure of the gas within the lumen 121. As depicted in FIG. 2B, the first rib 120 having a half cylinder shape in cross section has two wires 122a, 122b embedded therethrough and independently disposed outside the lumen 121, in which one wire may be designated to heat the respiratory gas in the tubular body 110, while the other wire is designated to detect the temperature, humidity and/or pressure of the respiratory gas in the tubular body 110 with the aid of a plurality of sensors (not depicted) disposed in or on the tubular body or at any position suitable for its purpose.

In non-limiting embodiments, the lumen 121 serves as an aeration channel allowing the exhaled gas and/or the inhaled gas of a subject to pass through, thus, is useful for monitoring parameters (e.g., temperature, pressure, flow rate, humidity and etc.) of the gas therein, and wherein the respiratory gas, also as a pressured gas, delivered from respiratory device 200 does not pass through the lumen 121 directly. Therefore, the channel of the tubular body 110 allowing the respiratory gas delivered from respiratory device 200 to pass through is different from that of the lumen 121. In one preferred embodiment, the parameter is the flow rate or the pressure of exhaled and/or inhaled gas from the subject, and the measured flow rate or the pressure value can be used as a reference value for the pressure in the nasal cavity of the subject.

Figure 2C:
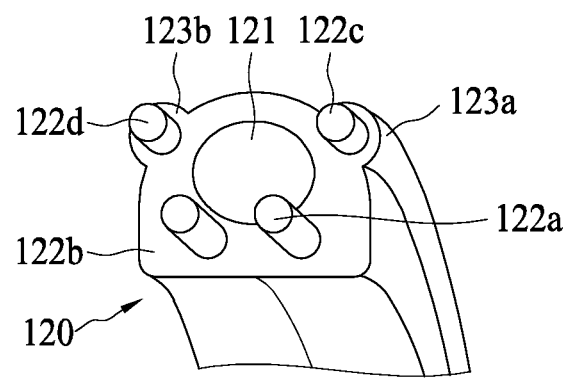
FIGS. 2C and 2D are respectively cross-sectional views of the first rib 120 in accordance with alternative embodiments of the present disclosure.
Figure 2D:
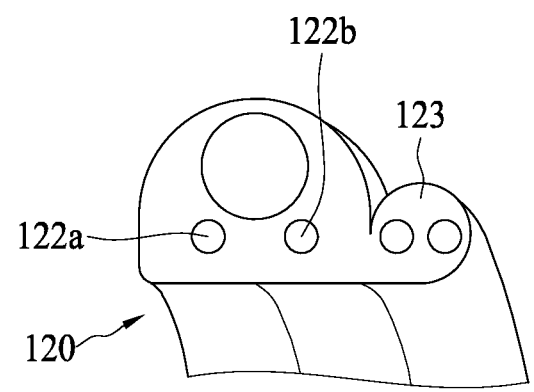

In alternative embodiments, the first rib 120 differs from the one in FIG. 2B in that it further includes one or more ridges 123 independently extending out from the top outer surface or one side of the first rib 120 (FIGS. 2C and 2D) and comprises two wires 122c, 122d therethrough. In the embodiment depicted in FIG. 2C, two ridges 123a, 123b respectively extended out from the outer surface of the first rib 120, and independently comprises a wire 122c, 122d therethrough. In the embodiment depicted in FIG. 2D, the first rib 120 differs from the one in FIG. 2B in that it further includes one ridge 123 extending out from one side of the outer surface of the first rib 120 and comprises two wires 122c, 122d therethrough. Note that it is not necessary for the ridge to comprise a wire therein, it some cases, the ridge may be free of any wires as opposed to that depicted in FIG. 2C or 2D.

Figure 3A:
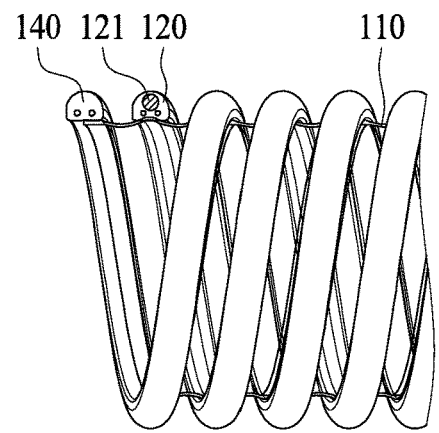
FIGS. 3A to 3C are respectively schematic drawings of a portion of the medical tube 100 of FIG. 2A depicting various combinations of the first and second ribs 120, 140 in cross section in accordance with certain embodiments of the present disclosure.
Figure 3B:
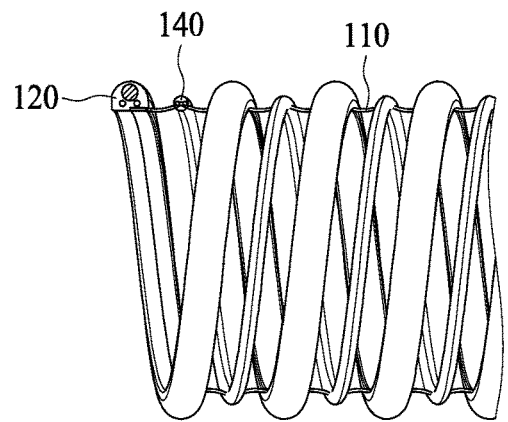
Figure 3C:
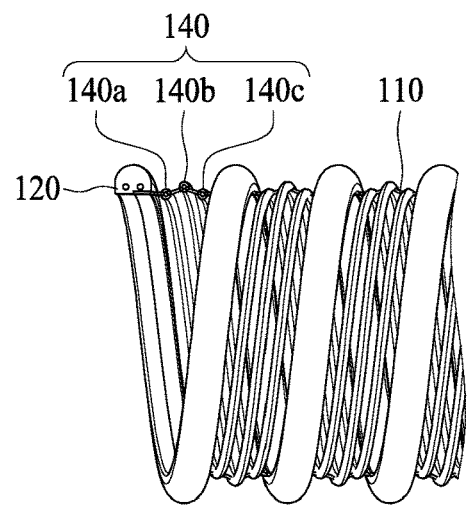

In further embodiments, in addition to the first rib 120, the medical tube 100 may further include one or more of a second ribs 140 (e.g., 1, 2, or 3 of the second rib) independently running parallel to the first rib 120 along the outer surface of the tubular body 110 (FIGS. 3A to 3C). The second rib 140 may be same or different from the first rib 120 in its shape, size, and/or structure. In both embodiments depicted in FIGS. 3A and 3B, the second rib 140 differs from the first rib 120 in that it does not have a lumen 121. Further, the second rib 140 depicted in FIG. 3B differs from the one in FIG. 3A in that it is much smaller in size. In the embodiment depicted in FIG. 3C, the medical tube 100 has one first rib 120 and three second ribs 140a, 140b and 140c, respectively parallel to each other and helically extending along the outer surface of the tubular body 110. Further, same as the one depicted in FIG. 3A or 3B, each of the second ribs 140a, 140b, 140c differs from the first rib 120 in that it does not have a lumen. Further, each of the first and second ribs may be integrally formed with the tubular body 110 or independently formed and removably wrapped around the outer surface of the tubular body 110.

Figure 4A:
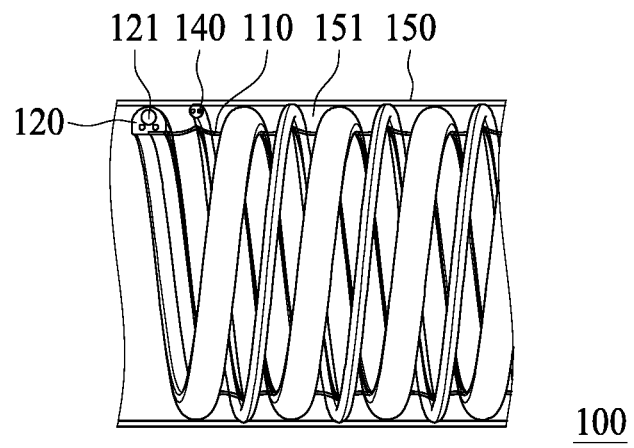
FIGS. 4A and 4B are schematic drawings of a portion of the medical tube 100 in accordance with further embodiments of the present disclosure.
Figure 4B:
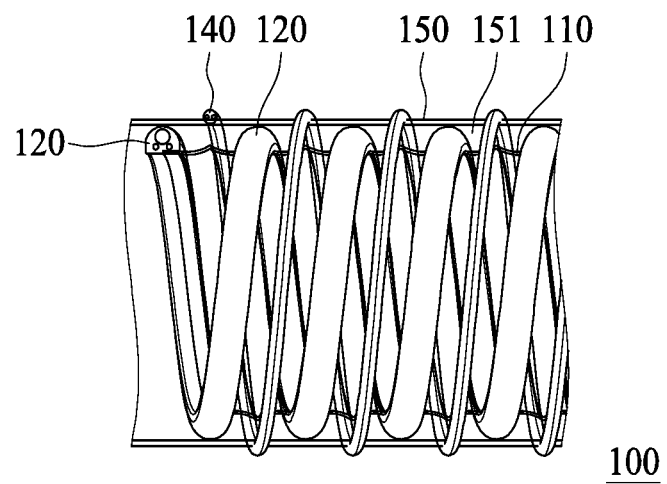

Additionally, the medical tube 100 may be encapsulated with a membrane 150 thereby embedding the first rib 120 and/or the second rib 140 in the membrane 150, while simultaneously creating a helical space 151 along the outer surface of the tubular body 110 (FIGS. 4A and 4B). Similar to the lumen 121 of the first rib 120, the helical space 151 also serves as an aeration channel allowing the exhaled gas and/or the inhaled gas of a subject to pass through, thus, is useful for monitoring parameters (e.g., temperature, pressure, flow rate, humidity and etc.) of the gas therein. According to one embodiment, the respiratory gas, also as a pressured gas, delivered from respiratory device 200 does not pass through the helical space 151; thus, the channel of the tubular body 110 allowing the respiratory gas delivered from respiratory device 200 to pass through is different from that of the helical space 151.

In the embodiment depicted in FIG. 4A, the tubular body 110 has both the first and second ribs 120, 140 wrapped around its outer surface before being encapsulated by the membrane 150, whereas in the embodiment depicted in FIG. 4B, the tubular body 110 having a first rib 120 wrapped around its outer surface is first encapsulated by the membrane 150 before being further wrapped with a second rib 140 along its outer surface. Accordingly, the first rib 120 is embedded within the membrane 150, while the second rib 140 is disposed on the membrane 150 and helically extended along the outer surface of the membrane encapsulated tubular body 110. In either embodiments of FIG. 4A or 4B, membrane encapsulation would generate a helical space 151 along the outer surface of the tubular body 110 thereby allowing the exhaled gas and/or the inhaled gas of a subject to be monitored during respiratory therapy, so as to determine whether sufficient amount of the respiratory gas has been delivered to the subject.

Figure 5A:
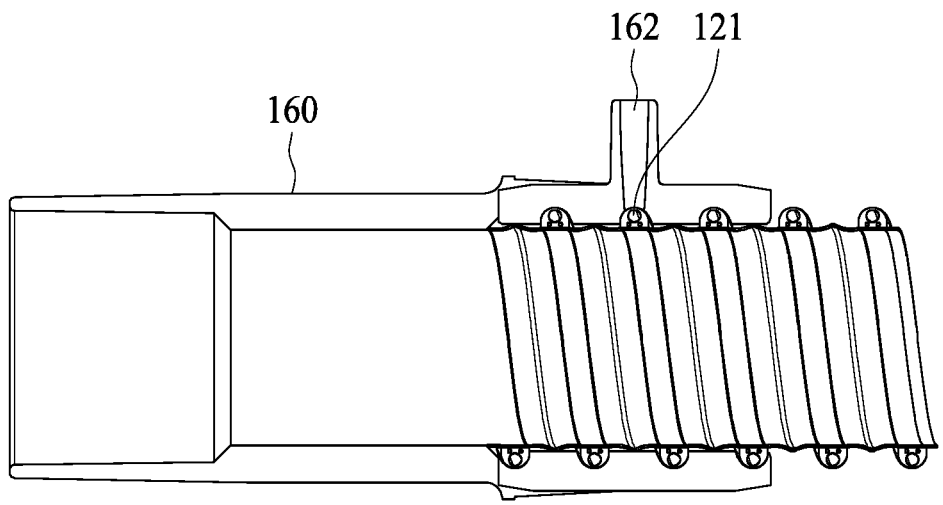
FIGS. 5A and 5B are schematic drawings of the medical tube 100 coupling with a joint tube 160 in accordance with some embodiments of the present disclosure.
Figure 5B:
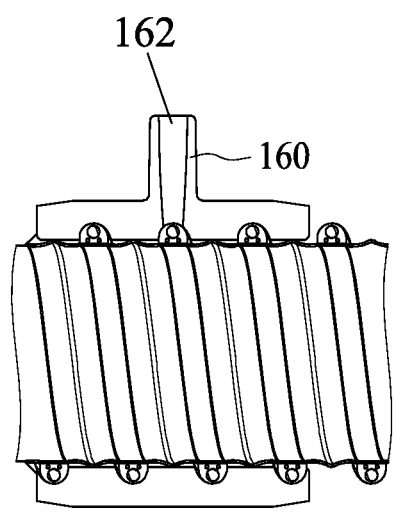

For the purpose of monitoring the exhaled gas and/or the inhaled gas of a subject sent from the respiratory device 200 during respiratory therapy, the medical tube 100 may further includes a joint tube 160 fluidly connecting to the lumen 121 of the first rib 120 or to the helical space 151 created by membrane encapsulation described in FIGS. 4A and 4B (FIGS. 5A to 5B), so as to monitor and/or determine the pressure or flow rate of an exhaled gas and/or the inhaled gas of a subject. Refer to FIGS. 5A and 5B, the joint tube 160 may be constructed in its body an aeration pipe 162, which is fluidly connected to the lumen 121 of the first rib 120 or to the helical space 151 created by membrane encapsulation described above, thereby allowing the flow rate or pressure of an exhaled gas and/or the inhaled gas of a subject to be determined. The joint tube 160 may have a size (e.g., length) covering at least, a portion of the tubular body having a first rib 120 helically extending along its outer surface, and a free end 112 of the tubular body 110 (FIG. 5A). Alternatively, the joint tube 160 may have a size just big enough to cover a portion of the tubular body having both the first rib 120 wrapped around the outer surface of the tubular body 110, but not the free end 112 of the tubular body 110 (FIG. 5B).

Additionally, the tubular body or the joint tube may be made of same or different material. Examples of the material suitable for making the tubular body and/or the joint tube include, but are not limited to, silicone, polypropylene (PP), polyethylene (PE), polycarbonate (PC), polyvinylchloride (PVC), polycaprolactone (PCL), acrylonitrile butadiene styrene (ABS), polysulfone (PSU), polycyclohexylenedimethylene terephthalate glycol (PCTG), thermoplastic elastomer (TPE), thermo polyurethane (TPU), thermoplastic vulcanizate (TPV), thermoplastic Styrene (TPS), thermoplastic polyester elastomer (TPEE), thermoplastic polyamide elastomer (TPA), HYTEL® and the like. In another embodiment, the material suitable for making the tubular body and/or the joint tube include, but are not limited to, foaming material.

2. Alternative Design of the Present Medical Tube

The medical device in this alternative design includes, a tubular body, a first rib helically wrapped around the outer surface of the tubular body, and a membrane encapsulating the first rib. Additionally, the medical tube in this embodiment may further include a joint tube coupling to the smoothbore end of the tubular body. The tubular body, the membrane, and the joint tube in this alternative design are same as that described in Section 1 of this paper, thus are not repeated herein for the sake of brevity, the first rib, however, differs from that in Section 1 (e.g., FIG. 2A) in that it is free of any lumen.

Figure 6A:
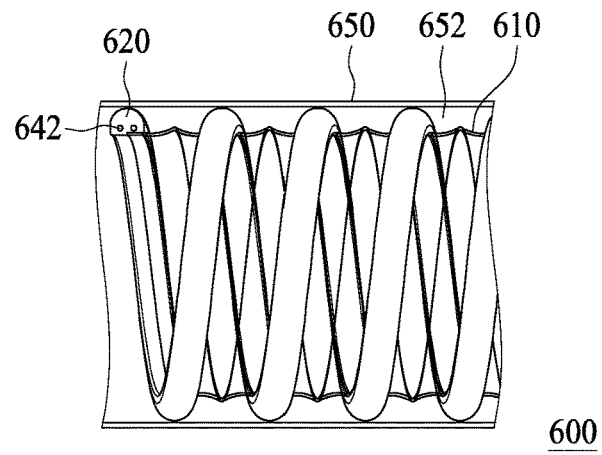
FIG. 6A is a schematic drawing of a portion of a medical tube 600 depicting the first rib 620 in cross section in accordance with one embodiment of the present disclosure.

Referring to FIG. 6A, which is a schematic diagram depicting a portion of a medical tube 600 bearing the alternative design of the first rib described herein. The medical tube 600 includes a tubular body 610, a first rib 620 helically extending along the outer surface of the tubular body 610, and a membrane 650 encapsulating the first rib 620 thereby creating a helical space 652 along the outer surface of the tubular body 610. In this embodiment, the first rib 620 is free of any lumen and includes in its structure, one or more wires 622 therethrough, which are independently configured to heat the respiratory gas within the tubular body 610, and/or to detect the temperature, humidity, flow rate or pressure of the respiratory gas within the tubular body 610. As depicted in FIG. 6A, the first rib 620 has two wires 642 extending the entire length of the first rib 620, in which one wire may be designated to heat the respiratory gas in the tubular body 610, while the other wire is designated to detect the temperature, humidity, flow rate and/or pressure of the respiratory gas in the tubular body 610 with the aid of a plurality of sensors (not depicted) disposed in or on the tubular body or at any position suitable for its purpose. The helical space 652 created by membrane encapsulation also serves as an aeration channel, similar to that of the helical space 152 described above in FIG. 4A or 4B, thus is not described herein for the sake of brevity.

Figure 6B:
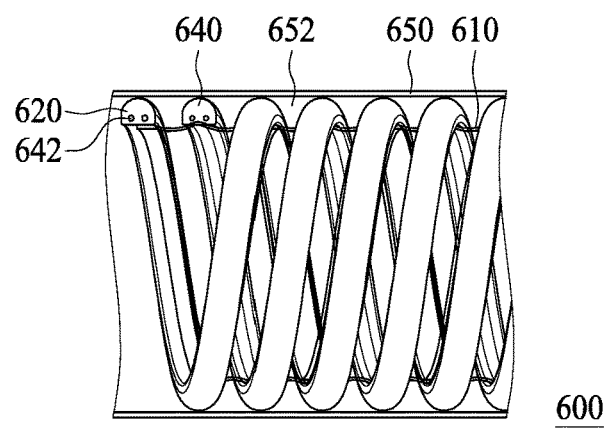
FIGS. 6B and 6C are respectively schematic drawings of a portion of a medical tube 600 depicting the first rib 620 and the second rib 640 in cross section in accordance with certain embodiments of the present disclosure.
Figure 6C:
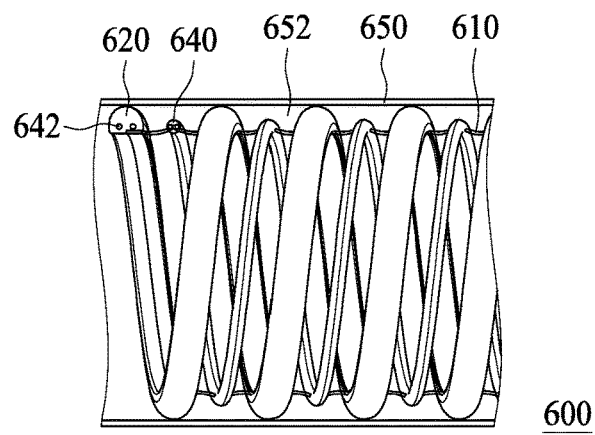

Additionally or alternatively, in addition to the first rib 620, the medical tube 600 may further include one or more of a second rib 640 (e.g., 1, 2, or 3 of the second rib) independently running parallel to the first rib 620 along the outer surface of the tubular body 610 (FIGS. 6B and 6C). The second rib 640 may be same or different from the first rib 620 in its shape, size, and/or structure. In the embodiments depicted in FIG. 6B, the second rib 640 is same as the first rib 620, while in the embodiment depicted in FIG. 6C, the second rib 640 differs from the first rib 620 in that it is much smaller in size. Further, like the first rib 620, each second rib 640 may comprise one or more wires 642 therethrough. Further, each of the first and second ribs may be integrally formed with the tubular body 610 or independently formed and removably wrapped around the outer surface of the tubular body 610.

Figure 7A:
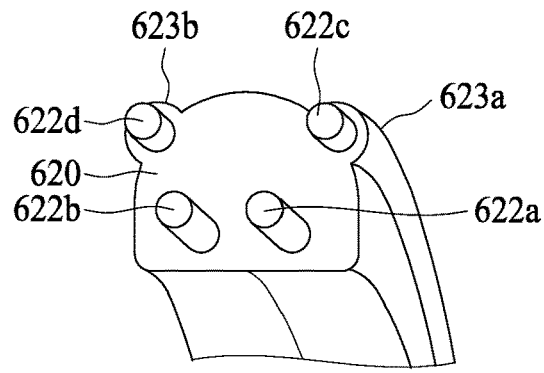
FIGS. 7A to 7C are cross-sectional views of various forms of the first rib 620 of the medical tube 600 in accordance with some embodiments of the present disclosure.
Figure 7B:
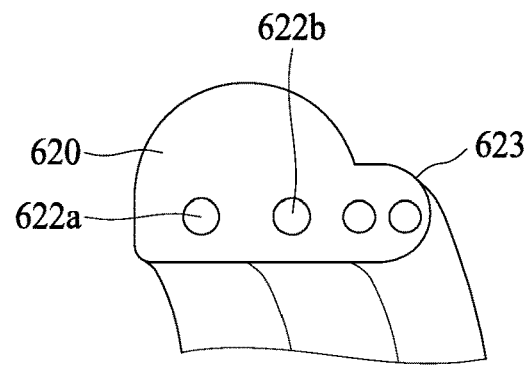

References are now made to FIGS. 7A and 7B, in which the first rib 620 differs from the one in FIG. 6A in that it further includes one or more ridges 623 independently extending out from the outer surface of the first rib 620. In the embodiment depicted in FIG. 7A, two ridges 623a, 623b respectively extended out from the top outer surface of the first rib 620, and independently comprises a wire 622c, 622d therethrough. The first rib 620 comprises two wires 622a, 622b therethrough. In the embodiment depicted in FIG. 7B, the first rib 620 differs from the one in FIG. 6A in that it further includes one ridge 623 extending out from one side of the outer surface of the first rib 620 and comprises two wires 622a, 622b therethrough. Note that it is not necessary for the ridge to comprise a wire therein, it some cases, the ridge may be free of any wires as opposed to that depicted in FIG. 7A or 7B.

Figure 7C:
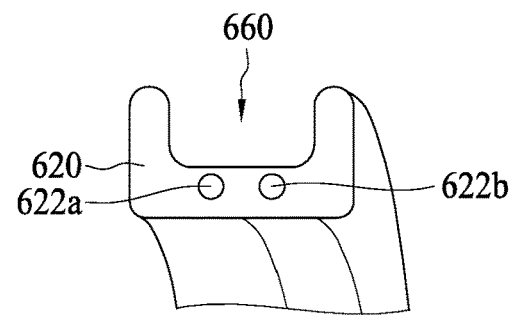

Referring to FIG. 7C, which depicts an alternative form of the first rib 620 suitable for use in the present medical tube 600. The first rib 620 in this embodiment has a trench 660 formed on one side of its body and extended through its entire length; and two wires 622*a*, 622*b* embedded therethrough.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A medical tube for delivering a respiratory gas to a subject, wherein the medical tube is in fluid connection with a user interface and a respiratory device, the medical tube comprises:
   a tubular body for delivering the respiratory gas from the respiratory device to the user interface;
   a first rib helically extending along the outer surface of the tubular body, in which the first rib comprises:
      at least one wire disposed within the first rib and is configured to heat the respiratory gas within the tubular body, and/or to detect the temperature, humidity, flow rate or pressure of the respiratory gas;
   a membrane encapsulating the first rib thereby generating a helical space along the outer surface of the tubular body; wherein the helical space serves as an aeration channel allowing the exhaled gas of the subject to pass through, and the respiratory gas delivered from respiratory device does not pass through the helical space;
   wherein the helical space is configured to monitor the temperature, pressure, flow rate or humidity of the exhaled gas of the subject; and
   a joint tube disposed at one of the free ends or the outer surface of the tubular body, wherein the joint tube is in fluid connection with the helical space.

2. The medical tube of the claim 1, wherein the first rib is free of any lumen.

3. The medical tube of the claim 1, wherein the first rib further comprises one or more ridges or a trench independently extending out from its outer surface.

4. The medical tube of claim 3, wherein the one or more ridges independently comprises one or more wires extending therethrough.

5. The medical tube of the claim 1, further comprising a second rib disposed next to the first rib, in which the second rib comprises at least one wire disposed within the second rib and is configured to heat the respiratory gas within the tubular body, and/or to detect the temperature, humidity, flow rate or pressure of the respiratory gas.

6. A respiratory system for use in a respiratory therapy of a subject comprising:
   the medical tube of claim 1;
   a user interface in fluid connection with the medical tube of claim 1; and
   a respiratory device fluidly and electrically connected with the medical tube of claim 1, wherein the respiratory device is configured to provide the respiratory gas and detect the flow rate or pressure of an exhaled gas and/or an inhaled gas of the subject within the helical space.

7. The respiratory system of the claim 6, wherein the first rib further comprises one or more ridges or a trench independently extending out from its outer surface.

8. The respiratory system of claim 6, further comprising a second rib disposed next to the first rib, in which the second rib comprises at least one wire disposed within the second rib and is configured to heat the respiratory gas within the tubular body, and/or to detect the temperature, humidity, flow rate or pressure of the respiratory gas.

* * * * *